(12) United States Patent
Goldman

(10) Patent No.: US 8,216,124 B2
(45) Date of Patent: *Jul. 10, 2012

(54) SYSTEMS AND METHODS FOR TREATING STRESS URINARY INCONTINENCE

(76) Inventor: Ian L. Goldman, Scottsdale, AZ (US)

( * ) Notice: Subject to any disclaimer, the term of this patent is extended or adjusted under 35 U.S.C. 154(b) by 488 days.

This patent is subject to a terminal disclaimer.

(21) Appl. No.: 12/430,824

(22) Filed: Apr. 27, 2009

(65) Prior Publication Data
US 2010/0113868 A1    May 6, 2010

Related U.S. Application Data

(60) Provisional application No. 61/095,231, filed on Nov. 3, 2008.

(51) Int. Cl.
*A61F 2/02* (2006.01)
*A61F 2/00* (2006.01)

(52) U.S. Cl. ............................................. 600/30; 600/29

(58) Field of Classification Search ............... 600/29–32; 606/151–156
See application file for complete search history.

(56) References Cited

U.S. PATENT DOCUMENTS

| | | | | |
|---|---|---|---|---|
| 7,056,333 B2 * | 6/2006 | Walshe | | 606/232 |
| 2002/0188169 A1 * | 12/2002 | Kammerer et al. | | 600/30 |
| 2003/0078604 A1 * | 4/2003 | Walshe | | 606/151 |
| 2006/0264950 A1 * | 11/2006 | Nelson et al. | | 606/72 |
| 2007/0032695 A1 * | 2/2007 | Weiser | | 600/29 |
| 2009/0076318 A1 * | 3/2009 | Li | | 600/30 |
| 2009/0221868 A1 * | 9/2009 | Evans | | 600/37 |
| 2010/0113866 A1 * | 5/2010 | Goldman | | 600/30 |
| 2010/0261950 A1 * | 10/2010 | Lund et al. | | 600/30 |
| 2011/0178365 A1 * | 7/2011 | Browning | | 600/30 |

FOREIGN PATENT DOCUMENTS

| | | | |
|---|---|---|---|
| GB | 2382993 B | * | 3/2005 |
| WO | WO 2010078591 A1 | * | 7/2010 |

OTHER PUBLICATIONS

A.M.I.® TVA Sling / TOA Sling. Product Group Urogynaecology. Issue Sep. 2005.*

* cited by examiner

*Primary Examiner* — Miranda Le
*Assistant Examiner* — Meredith Weare
(74) *Attorney, Agent, or Firm* — Allen J. Moss; Squire Sanders (US) LLP

(57) ABSTRACT

Systems and methods are delineated for treating urinary incontinence (UI). An exemplary system comprises a strip of mesh having a primary axis and a secondary axis orthogonal to the primary axis; a first end and a second end, the first end and the second end located at opposite ends of the primary axis; and a first surface located on a first side of the strip, the first surface for providing support to the urethra of a patient under treatment for UI. The system also includes a first fastener including at least one barb coupled to the first end of the strip and a second fastener including at least one barb coupled to the second end of the strip. The system also includes a plurality of cords coupled to the strip for extracting the strip when desired.

23 Claims, 10 Drawing Sheets

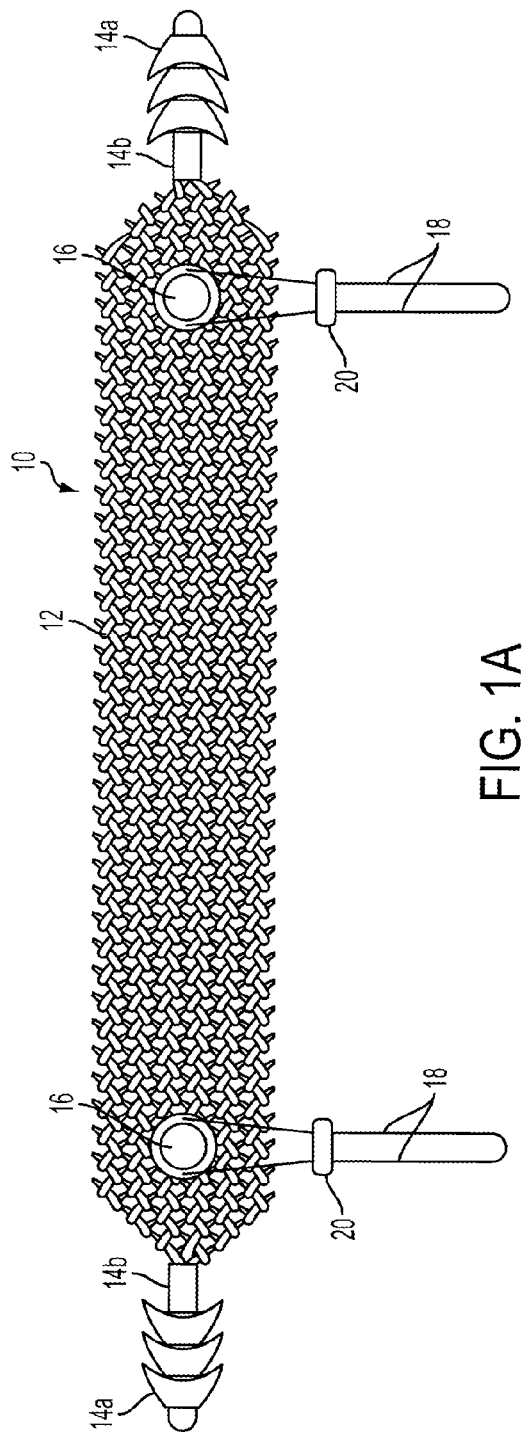
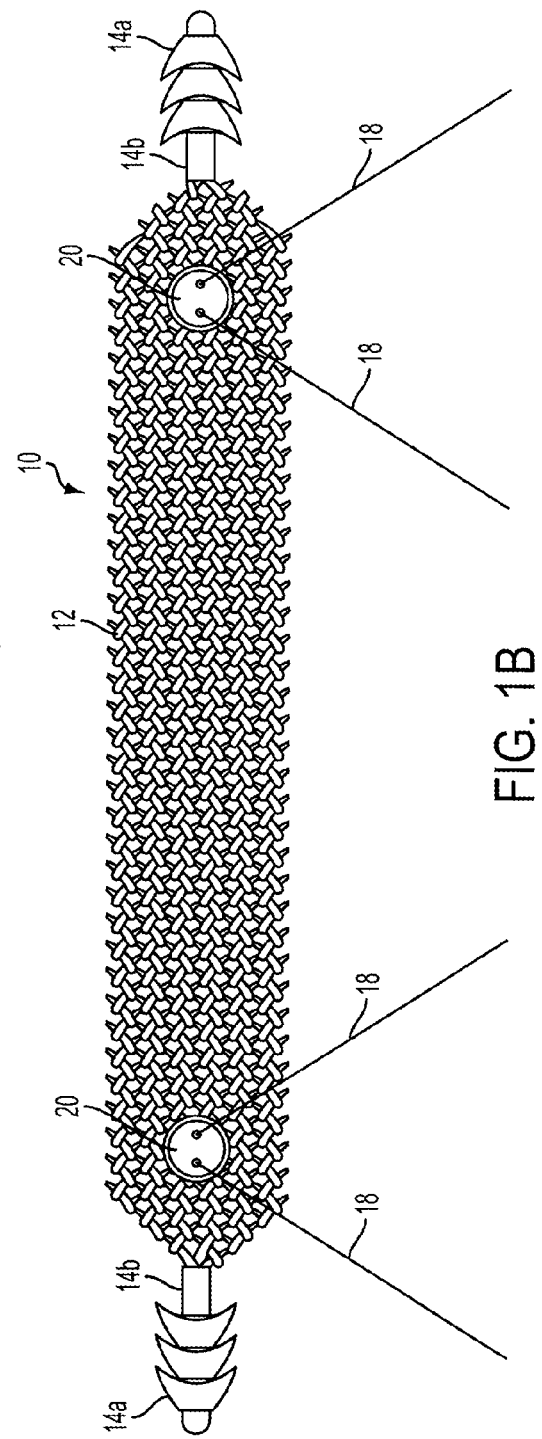

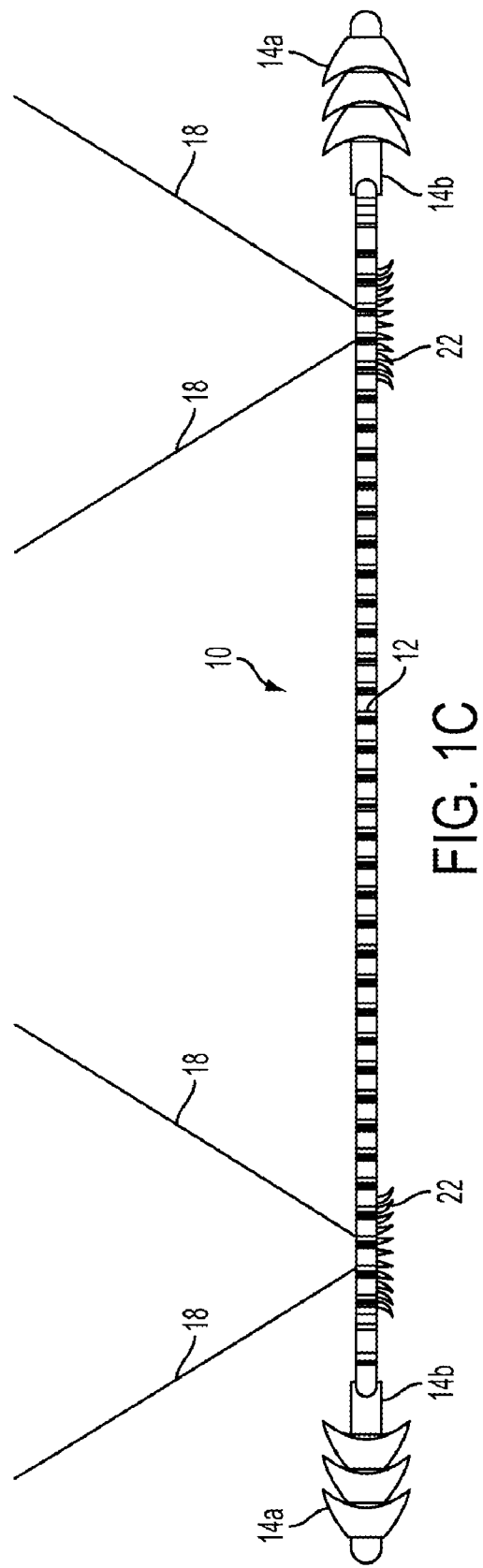

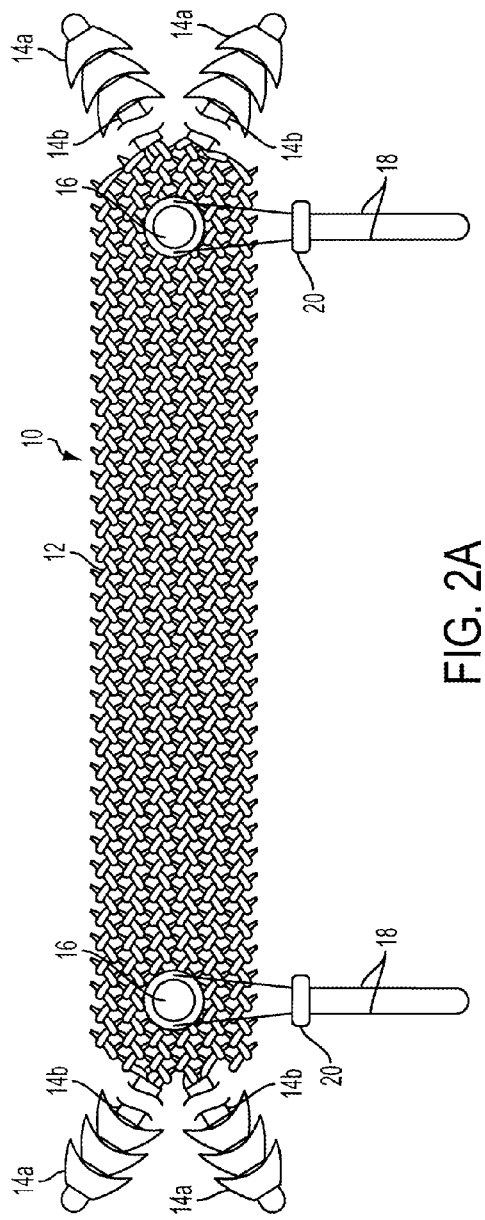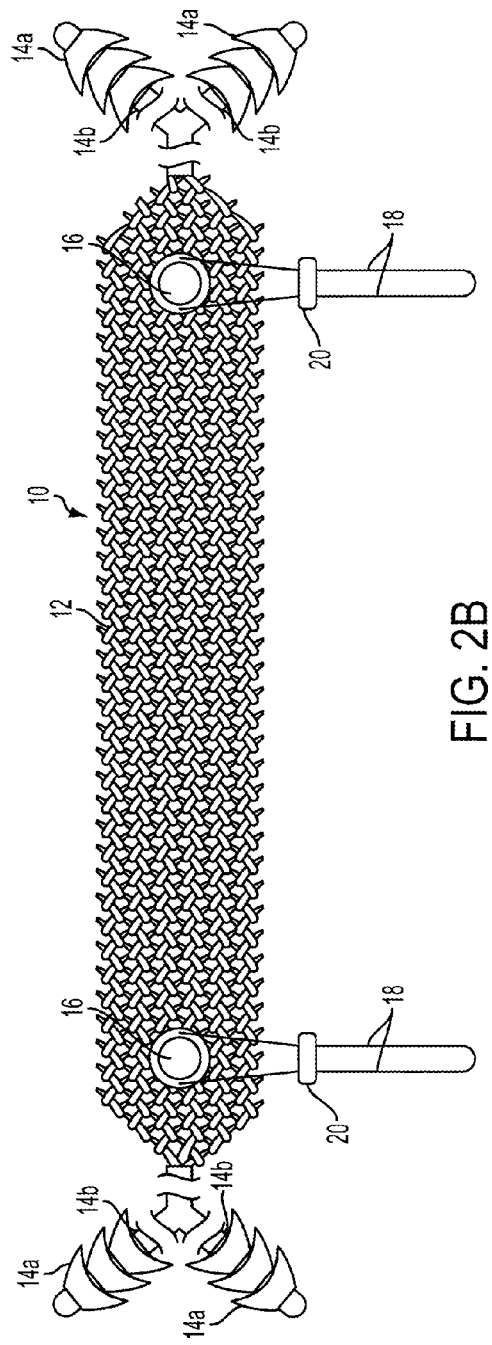
FIG. 2A
FIG. 2B

SYSTEMS AND METHODS FOR TREATING STRESS URINARY INCONTINENCE

CROSS REFERENCED TO RELATED APPLICATION

This application is related and claims priority to U.S. Provisional Application No. 61/095,231, filed Nov. 3, 2008, and entitled "Systems and Methods for Treating Stress Urinary Incontinence."

BACKGROUND OF THE INVENTION

1. Field of the Invention

The present invention relates to urinary incontinence and, more particularly, to systems and methods for treating stress urinary incontinence.

2. Description of the Related Art

Urinary incontinence (UI) is any involuntary leakage of urine. It is a common and distressing problem that may have a profound impact on quality of life. UI often results from an underlying treatable medical condition.

Continence and urination involve a balance between urethral closure and detrusor muscle activity. Urethral pressure normally exceeds bladder pressure, resulting in urine remaining in the bladder. The proximal urethra and the bladder are both within the pelvis. Intra-abdominal pressure increases, e.g., from coughing and sneezing, are typically transmitted to both the urethra and the bladder equally, leaving the pressure differential unchanged, resulting in continence. Normal urination is the result of changes in both of these pressure factors, i.e., urethral pressure decreasing and bladder pressure increasing.

UI affects women of all ages, however, UI is highly prevalent in women across their adult life span and its severity increases linearly with age. Up to 35% of the total population over the age of 60 years is estimated to have UI, with women twice as likely as men to experience UI. One in three women over the age of 60 years are estimated to have UI.

A leading form of UI is known as stress urinary incontinence (SUI). SUI is essentially due to pelvic floor muscle weakness. It results in a loss of small amounts of urine with coughing, laughing, sneezing, exercising or other movements that increase intra-abdominal pressure and thus increase pressure on the bladder. Physical changes resulting from pregnancy, childbirth and menopause often cause SUI.

The urethra is supported by fascia of the pelvic floor. If the fascial support is weakened, as it can be from pregnancy, childbirth or normal physiological changes in the body over the course life, the urethra can move downward at times of increased abdominal pressure, resulting in SUI.

A surgical procedure for treating SUI employs what is commonly referred to as a sling. A sling may consist of any desired material in any desired shape but often consists of a synthetic mesh material or a mesh of biomaterial, e.g., bovine, porcine or the patients' own tissue, in the shape of a ribbon that is placed under the urethra. In practice, a sling surgically implanted beneath a patient's urethra replaces the deficient pelvic floor muscles and provides structural support under the urethra that is sufficient to limit or eliminate SUI.

A common surgical procedure for implanting a sling is referred to as the transobturator procedure. With this procedure, a pair of incisions are made near the groin at the level of the obturator fossa of the pelvic bone and one in the vagina. Sling carriers are passed through from the groin incisions to the vaginal incision. Extension arms connected to the sling are fixedly attached to the sling carriers and the sling carriers are moved to withdraw the extension arms from the pair of incisions made near the groin and to position the sling under the urethra. Thereafter, the extension arms are cut to free the sling carriers, sling tension is adjusted and the incision is closed.

The transobturator procedure involves passing the sling carriers from the two incisions made near the groin at the obturator of the pelvic bone to the vaginal incision. By necessity then, the sling carriers pass through the patient, increasing patient trauma that may include nerve damage. To limit such patient trauma, a less invasive surgical procedure has emerged in which a sling is implanted but only a single vaginal incision is required. However, existing slings, whether implanted using only a vaginal incision or the multiple-incision transobturator procedure, have further limitations, including the inability to reposition the sling.

For example, some current slings include an anchoring mechanism, such as a barbed fastener located at each end of the sling for implanting into the patient's tissue. The anchoring mechanism provides holding strength for the sling until post-surgical tissue growth enables the patient's tissue to provide supplemental long-term holding strength for the sling. It is not uncommon for a surgeon to improperly implant the sling, i.e., when device placement is not optimum for treatment of SUI. At such times, the surgeon must completely remove the sling from the patient and attempt to properly implant the removed sling.

To remove an improperly placed sling, a surgeon typically uses his or her hand, a surgical tool, e.g. a hemostat, or some combination thereof to grasp a portion of the sling and remove it from the patient. The process for removing the sling, once implanted in the patient, is difficult because it is not easy for the surgeon to see and grasp the implanted sling. Moreover, assuming the surgeon can even see or locate an improperly implanted sling, the surgeon must grasp whatever portion of the sling that he or she can to remove the device. Typically, the surgeon grasps an improperly implanted sling at a single position somewhere on the sling and employs considerable force to remove the device. The process of removing an improperly implanted sling using such considerable retraction force applied to a single position on the sling often damages the device. Specifically, the sling is often stretched or torn such that it cannot be reused. In such instances, the surgeon must use another sling to complete the procedure, resulting in increased cost for the procedure.

Even for slings that do not include an anchoring mechanism, such as a barbed fastener located at each end of the sling, device removal is an issue for an improperly implanted sling. In such instances, following device implantation with the transobturator procedure, the sling carriers which are fixed to the sling extension arms cannot be backed out to remove the sling from beneath the urethra. Accordingly, it is not possible to remove the sling for repositioning, if desired.

Existing slings also have limited holding strength. As noted above, post-surgical tissue growth enables the patient's tissue to provide supplemental long-term holding strength for the sling. However, until such time that post-surgical tissue growth enables the patient's tissue to provide supplemental long-term holding strength for the sling, means for providing preliminary holding strength are employed. Such preliminary holding strength systems include those which employ an anchoring mechanism, such as a barbed fastener located at each end of the sling, for implanting into the patient's tissue. Other slings do not employ an anchoring mechanism and simply rely on a friction fit between the sling and the patient's tissue to hold the sling in place. Regardless of the type of preliminary holding strength system that is employed, current slings continue to move following surgery, and therefore, would benefit from improved holding strength.

A need exists for systems and methods for treatment of SUI, which overcome these and other problems associated with the prior art.

SUMMARY OF THE INVENTION

In accordance with an embodiment of the present invention, a system is disclosed for treating urinary incontinence (UI), the system comprising a strip of mesh having a primary axis and a secondary axis orthogonal to the primary axis; a first end and a second end, the first end and the second end being located at opposite ends of the primary axis; a first surface located on a first side of the strip, said first surface for providing support to the urethra of a patient under treatment for UI; and a second surface located on a second side of the strip opposite the first surface; a first fastener including at least one barb, said first fastener coupled to the first end of the strip; a second fastener including at least one barb, said second fastener coupled to the second end of the strip; and a plurality of cords, each cord of the plurality of cords coupled to the strip for extracting the strip when desired.

In accordance with another embodiment of the present invention, a system is disclosed for treating urinary incontinence (UI), the system comprising a sling for providing support to the urethra of a patient under treatment for UI; a first fastener coupled to a first end of the strip; a second fastener coupled to a second end of the strip; and a plurality of cords, each cord of the plurality of cords coupled to the strip for extracting the strip when desired.

In accordance with yet another embodiment of the present invention, a method is disclosed for treating urinary incontinence (UI), the method comprising providing a sling for providing support to the urethra of a patient under treatment for UI; the sling including a first fastener coupled to a first end of the strip; a second fastener coupled to a second end of the strip; and a plurality of cords, each cord of the plurality of cords coupled to the strip for extracting the strip when desired.

In accordance with still another embodiment of the present invention, a method is disclosed for treating urinary incontinence (UI), the method comprising removing from a patient a sling for providing support to the urethra of the patient under treatment for UI; and reusing the removed sling for providing support to the urethra of the patient under treatment for UI.

In accordance with yet another embodiment of the present invention, a method is disclosed for treating urinary incontinence (UI), the method comprising providing a reusable sling for providing support to the urethra of a patient under treatment for UI, the reuse of the sling following the removal of the sling from the patient.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1A is a plan view of an embodiment of a medical device for use in treatment of urinary incontinence (UI), in accordance with systems and methods consistent with the present invention.

FIG. 1B is a plan view of the embodiment of the medical device shown in FIG. 1A, in accordance with systems and methods consistent with the present invention. FIGS. 1A and 1B together show part of a sequence for assembly of the medical device.

FIG. 1C is a side elevation view of the embodiment of the medical device shown in FIG. 1B, in accordance with systems and methods consistent with the present invention.

FIGS. 1D and 1E together show part of a sequence for assembly of the medical device.

FIG. 2A is a plan view of another embodiment of a medical device for use in treatment of UI, in accordance with systems and methods consistent with the present invention.

FIG. 2B is a plan view of another embodiment of a medical device for use in treatment of UI, in accordance with systems and methods consistent with the present invention.

FIGS. 4F-4H show exemplary tools for inserting and/or extracting a fastener.

DESCRIPTION OF THE EMBODIMENTS

Figure 1D:
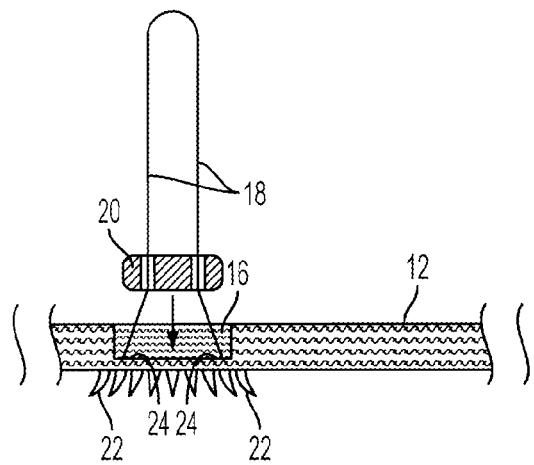
FIGS. 1D and 1E are partial cross-sectional views taken along line D-D of FIG. 1F, in accordance with systems and methods consistent with the present invention.

Reference will now be made in detail to the present exemplary embodiments of the invention, examples of which are illustrated in the accompanying drawings.

Referring to FIG. 1A, a plan view is shown of an embodiment of a medical device (or system) 10 for use in treatment of urinary incontinence (UI), in accordance with systems and methods consistent with the present invention. Medical device 10 comprises what those skilled in the art would refer to as an enhanced sling for treatment of UI. Those skilled in the art also recognize that a sling, such as medical device 10, may be successful for treating stress urinary incontinence (SUI) and any other type of UI, now known or later discovered.

Moreover, those skilled in the art understand that a sling, such as medical device 10, may be surgically implanted using a well known and minimally invasive procedure employing the insertion of a sling into a single vaginal incision. This procedure involves inserting a sling, such as medical device 10, into the vaginal incision, positioning the sling under the patient's urethra and anchoring the ends of the sling into the patient's tissue to provide support to the urethra. When such urethral support is applied at the correct position, a sling, such as medical device 10, can successfully ameliorate UI. As the details of this surgical procedure are well known, further details of the procedure are deemed unnecessary to understand the present invention and are therefore not set forth here.

Still with reference to FIG. 1A, medical device 10 may include a strip 12, one or more fasteners 14 (collectively, elements 14a and 14b), one or more apertures 16, one or more aperture covers 20 and one or more cords 18.

Strip 12 may comprise any material now known or later discovered for making slings that may be employed to treat UI. For example, strip 12 may comprise a synthetic mesh material, a mesh of biomaterial or a combination thereof. As is the case with current slings, regardless of the material employed to fabricate strip 12, strip 12 requires some degree of flexibility. For example, strip 12 should have enough flexibility to permit the ends of strip 12 to be anchored above the center of strip 12, essentially providing a curved, hammock-like structure to support a portion of the patient's urethra. At the same time, however, strip 12 should also provide rigidity suitable to support the patient's urethra. In general, strip 12 may have rigidity and flexibility consistent with now known or later discovered slings that may be employed to treat UI.

Strip 12 may have any desired shape and dimensions, however, in an exemplary embodiment, strip 12 may have a length in the range of 7 cm to 9 cm, a width in the range of 1 cm to 2 cm and a thickness in the range of 0.5 mm to 1 mm. Those skilled in the art understand that the aforementioned dimensions may extend outside the recited ranges for any reason, if so desired. For example, a larger patient may require a strip 12 of longer, wider and/or thicker dimensions. The ends of strip 12 may be tapered, as shown, tapered to a different degree or not tapered at all.

Figure 1E:
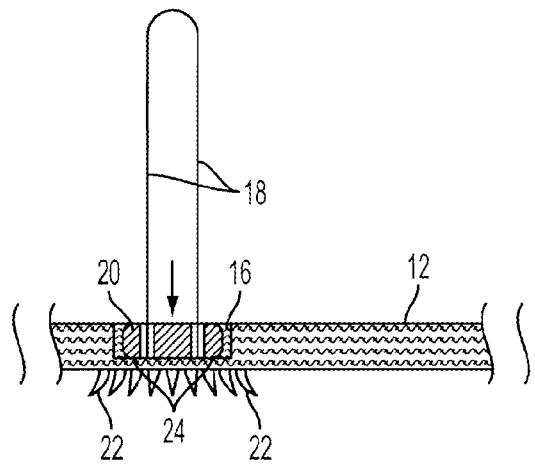

Strip 12 includes a primary axis, which is not labeled in FIG. 1A but extends lengthwise along the center of strip 12. Strip 12 also includes a secondary axis, which is also not labeled but extends widthwise (or vertically in FIG. 1A) and crosses the center of strip 12. Continuing with the hammock analogy set forth above, during surgical implantation, strip 12 is generally placed such that the patient's urethra rests orthogonally with respect to the primary axis. To be clear, this arrangement is not analogous to a person sleeping in a hammock in which case the person rests in alignment with the length of the hammock. The surface of strip 12 that is shown in FIG. 1A is not the urethra resting surface; the opposite side of strip 12, as shown in FIGS. 1C-1E, provides the urethra resting surface.

Still with reference to FIG. 1A, medical device 10 may also include one or more fasteners 14. As shown, medical device 10 may include a pair of fasteners 14, one coupled to each end of strip 12. Fasteners 14 may comprise any structure suitable for anchoring the ends of strip 12 into a patient's tissue, thereby providing support to the patient's urethra with strip 12. Fasteners 14 may also be made from any material suitable for patient implantation and anchoring the ends of strip 12 into patient tissue, such as a plastic, a metal, a composite or any combination thereof suitable for patient implantation.

In an exemplary embodiment, fasteners 14 may include a shaft 14b coupled to an end of strip 12 and one or more barbs 14a coupled to shaft 14b. As shown in FIG. 1A, fasteners 14 include a plurality of barbs 14a, however, a single barb 14a may be employed. Moreover, fasteners 14 are not limited to the structure, as shown in FIG. 1A. Rather, fasteners 14 may employ any structure suitable for anchoring the ends of strip 12 into patient tissue.

Additionally, and as will be discussed in detail below, fasteners 14 may be retractable. More specifically, fasteners 14 may have selectable positions. For example, fasteners 14 may include a first position in which the barb 14a or barbs 14a are extended, as shown in FIG. 1A, for anchoring into patient tissue, and a second position in which the barb 14a or barbs 14a are retracted to minimize tissue trauma when fastener 14 is removed from the patient's tissue. Moreover, it may be desirable to have the barb 14a or barbs 14a retracted during implanting of medical device 10. While an exemplary embodiment for providing a retractable fastener 14 is set forth below in connection with the description of FIGS. 4C-4E, those skilled in the art understand that fasteners 14 may be constructed in any one of a variety of different ways to provide a retractable fastener.

Again with reference to FIG. 1A, medical device 10 may also include one or more apertures 16, one or more aperture covers 20 and one or more cords 18.

The one or more apertures 16 may take any shape or size and may be positioned anywhere along strip 12. In an exemplary embodiment, however, strip 12 may include a pair of apertures 16, each being located closer to a respective end of strip 12 than to the opposing end of strip 12. For example, as shown in FIG. 1A, apertures 16 are located in proximity to the two ends of strip 12. As also shown in FIG. 1A, apertures 16 may be circular in shape and include a diameter larger than the diameter of the smaller spaces between the mesh strands forming strip 12.

As shown in FIGS. 1D and 1E, strip 12 may provide an extension or support shelf 24 within each aperture 16 that provides a seating surface for a corresponding aperture cover 20. Support shelves 24 may also provide locations where the ends of cords 18 may be fixedly attached. For each aperture 16 shown in FIG. 1A, a cord 18 may extend through the apertures in aperture cover 20 and be fixedly attached at both ends to the respective support shelf 24. Cords 18 may be made from any material suitable for patient implantation, such as a plastic, a metal, a composite or any combination thereof suitable for patient implantation.

The one or more apertures 16, one or more aperture covers 20 and one or more cords 18 collectively provide two separate functions for medical device 10. First, they enable the medical practitioner to remove an improperly placed strip 12, without damaging strip 12. For example, as noted for each aperture 16 shown in FIG. 1A, a cord 18 may extend through the apertures in an aperture cover 20 and be fixedly attached at both ends to a respective support shelf 24. Accordingly, if a medical practitioner is dissatisfied with the placement of strip 12, once it is anchored to the patient with fasteners 14, the practitioner may grasp aperture covers 20 (either by hand or with a suitable surgical instrument) and pull back on aperture covers 20 to remove fasteners 14 from patient tissue. Unlike prior art systems, this may be done without damaging strip 12, thereby permitting reuse of the same strip 12. Moreover, in embodiments of medical device 10 with 14 retractable fasteners 14, the barb 14a or barbs 14 may be retracted 14 prior to removal of strip 12 to minimize patient trauma.

A second function of medical device 10 that is collectively provided by the one or more apertures 16, one or more aperture covers 20 and one or more cords 18 is the ability to provide additional holding support for strip 12. For example, assuming that the medical practitioner has anchored strip 12 to a desired position, the practitioner may cut each cord 18 (approximately at its midpoint), slide aperture covers 20 along their respective cords 18 and tie cords 18 snugly against their respective aperture covers 20 such that aperture covers 20 press firmly against respective support shelves 24, creating a force applied against the patient's tissue to help hold medical device 10 in place (hereinafter the "seating force"). Aperture covers 20 may be made from any desired material that is suitable for patient implantation and more rigid than strip 12, such as a plastic, a metal, a composite or any desired combination thereof. This rigidity differential between aperture cover 20 and strip 12 improves the effectiveness of the seating force holding medical device 10 in place.

Additionally, as shown in FIG. 1C, an array of protrusions 22 may extend from strip 12 in proximity to apertures 16. As such, the seating force will be applied near the array of protrusions 22, which should further enhance the effectiveness of the seating force holding medical device 10 in place. The array of protrusions 22 may take any form or shape. As shown in FIGS. 1C-1E, the array of protrusions 22 is circular and arranged in proximity to the perimeter of apertures 16, though the array of protrusions 22 may take any other desired shape and may or may not reside in proximity to the perimeter of apertures 16. The protrusions forming array 22 are in a curved shape bending outwardly with respect to apertures 16. Those skilled in the art understand, however, that any other shape or arrangement may be employed for the protrusions forming array 22, such as inwardly bending protrusions. The protrusions comprising array 22 may comprise any material suitable for patient implantation and for supplementing the holding support for medical device 10 such as a plastic, a metal, a composite or any combination thereof.

In an exemplary embodiment of medical device 10, medical device 10 comprises an integral device in that the strip 12, the one or more fasteners 14, the one or more apertures 16, the one or more aperture covers 20 and the one or more cords 18 are all fabricated into a single device in which no additional parts are required (although there may be tools, which are not part of the medical device 10, that may be employed to insert and/or remove medical device 10). In a variation of medical device 10, medical device 10 may comprise an integral device except for the following distinction, namely, that the cords 18, as shown in FIG. 1A, would be precut, such that each cord 18 would have an end attached to a respective support shelf 24 and an opposite free end. In this instance, the aperture covers 20 would not be held by a closed loop of a cord 18; instead the medical practitioner would thread each cord 18 into the respective apertures in the aperture covers 20 when he was ready to synch down the aperture covers 20 and tie them in place with the cords 18. Thus, in this variation, medical device 10 may be considered an integral device, except for the aperture covers 20, which are separate and installed during the surgical procedure.

Referring to FIG. 1B, a plan view is shown of the embodiment of medical device 10 shown in FIG. 1A. FIGS. 1A and 1B together show part of a sequence for assembly of medical device 10. In FIG. 1B, we assume that fasteners 14 are anchored in patient tissue and the medical practitioner is satisfied with device placement. Accordingly, the practitioner has cut each cord 18 (assuming the integral embodiment of medical device 10) and slid aperture covers 20 along their respective cords 18 in preparation to tie cords 18 snugly against their respective aperture covers 20, creating the seating force to help hold medical device 10 in place. We note for the sake of clarity, however, that no patient is shown and that the angular positioning of medical device 10 does not reflect what angular positioning would actually look like installed in a patient (e.g., fasteners 14 would be canted up, instead of lying flat, as shown).

Referring to FIG. 1C, a side elevation view is shown of the embodiment of medical device 10 of FIG. 1B. As in FIG. 1B, we assume that fasteners 14 are anchored in patient tissue and the medical practitioner is satisfied with device placement. Accordingly, the practitioner has cut each cord 18 (assuming the integral embodiment of medical device 10) and slid aperture covers 20 along their respective cords 18 in preparation to tie cords 18 snugly against their respective aperture covers 20, creating the seating force to help hold medical device 10 in place. Again, we note for the sake of clarity, however, that no patient is shown and that the angular positioning of medical device 10 does not reflect what angular positioning would actually look like installed in a patient (e.g., fasteners 14 would be canted up, instead of lying flat, as shown).

Referring to FIGS. 1D and 1E, partial cross-sectional views are shown of the embodiment of medical device 10 in FIG. 1B. FIGS. 1D and 1E together show the seating of aperture cover 20 against support shelf 24. In FIG. 1D, the ends of cord 18 are shown fixedly attached to support shelf 24. FIG. 1D also shows that the attachment points for cord 18 are not aligned with the apertures in aperture cover 20, though they could be, if desired, however, having a slight alignment offset improves the holding strength once cord 18 is severed and tied down against aperture cover 20. It also bears mentioning that the space between the outer edge of aperture cover 20 and the wall forming aperture 16 may be exaggerated, i.e., there may be a snug mechanical fit between the outer edge of aperture cover 20 and the wall forming aperture 16.

Alternatively, there may be a small space between the outer edge of aperture cover 20 and the wall forming aperture 16. Additionally, whether there is a space or a snug mechanical fit between the outer edge of aperture cover 20 and the wall forming aperture 16, various additional mechanical interfaces may be employed. For example, a ring or other protrusion (not shown) may extend slightly from the outer edge of aperture cover 20 and a corresponding notch (not shown) may be produced in the wall forming aperture 16, such that the ring or other protrusion mates with the notch to provide a tactile sensation to the medical practitioner when aperture cover 20 is in place (prior to tying cords 18). Similarly, one or more posts or other protrusions (not shown) may extend slightly from the bottom surface of aperture cover 20 for mating with one or more corresponding apertures (not shown), which may be produced in support shelf 24, such that the one or more posts or other protrusions provide a tactile sensation to the medical practitioner when aperture cover 20 is in place, as well as assisting in proper alignment of aperture cover 20.

Figure 1F:
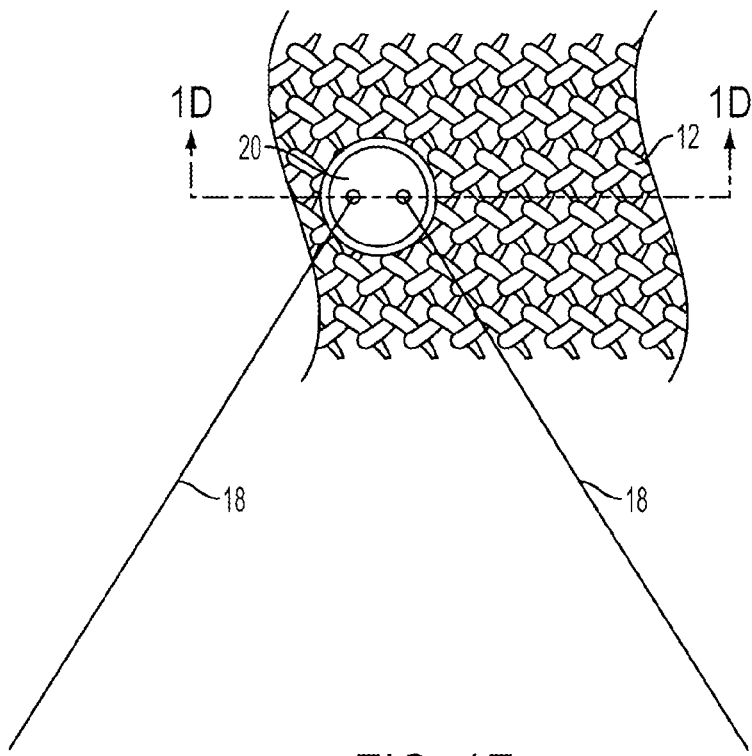
FIG. 1F is a partial plan view of the embodiment of the medical device shown in FIG. 1B, in accordance with systems and methods consistent with the present invention.

Referring to FIG. 1F, a partial plan view is shown of the embodiment of medical device 10 shown in FIG. 1B. In this view, the practitioner has cut cord 18 (assuming the integral embodiment of medical device 10) and slid aperture cover 20 along cord 18 in preparation to tie cords 18 snugly against aperture cover 20, creating the seating force to help hold medical device 10 in place. In this view, it is clear that the diameter of aperture 16 exceeds the diameter of any aperture in the regular pattern of apertures formed by the mesh strands in strip 12.

Referring to FIG. 2A, a plan view is shown of another embodiment of medical device 10 for use in treatment of UI, in accordance with systems and methods consistent with the present invention. The embodiment of medical device 10 shown in FIG. 2A differs from the embodiment shown in FIGS. 1A-1F by including more than one fastener 14 on each end of strip 12. Moreover, in the embodiment of medical device 10 shown in FIG. 2A, each fastener 14 has an independent shaft 14b connected to an end of strip 12. The use of multiple fasteners 14 on one or more ends of strip 12 may be called for in certain circumstances. For example, a larger patient having a larger pelvis may require more support that may be provided through use of multiple fasteners 14 on one or more ends of strip 12.

Referring to FIG. 2B, a plan view is shown of another embodiment of medical device 10 for use in treatment of UI, in accordance with systems and methods consistent with the present invention. The embodiment of medical device 10 shown in FIG. 2B differs from the embodiment shown in FIGS. 1A-1F by including more than one fastener 14 on each end of strip 12. Moreover, in the embodiment of medical device 10 shown in FIG. 2B each fastener 14 has an independent shaft 14b connected to a common member that is connected to an end of strip 12. Again, the use of multiple fasteners 14 on one or more ends of strip 12 may be called for in certain circumstances.

Figure 3A:
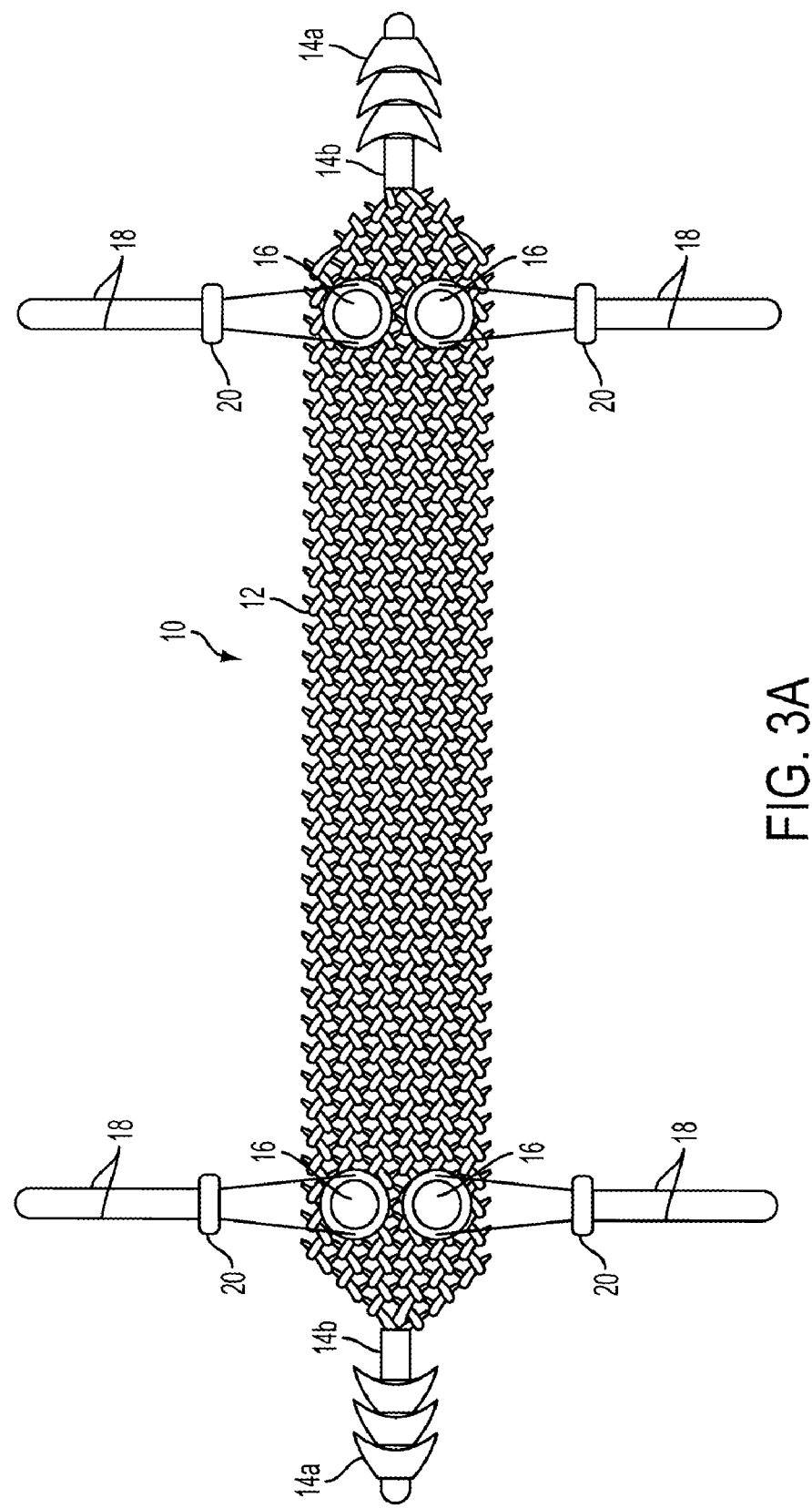
FIG. 3A is a plan view of another embodiment of a medical device for use in treatment of UI, in accordance with systems and methods consistent with the present invention.

Referring to FIG. 3A, a plan view is shown of another embodiment of medical device 10 for use in treatment of UI, in accordance with systems and methods consistent with the present invention. The embodiment of medical device 10 shown in FIG. 3A differs from the embodiment shown in FIGS. 1A-1F by including more than one aperture 16, more than one aperture cover 20 and more than one cord 18 in proximity to each end of strip 12. The use of more than one aperture 16, more than one aperture cover 20 and more than one cord 18 in proximity to each end of strip 12 may be called for in certain circumstances.

Figure 3B:
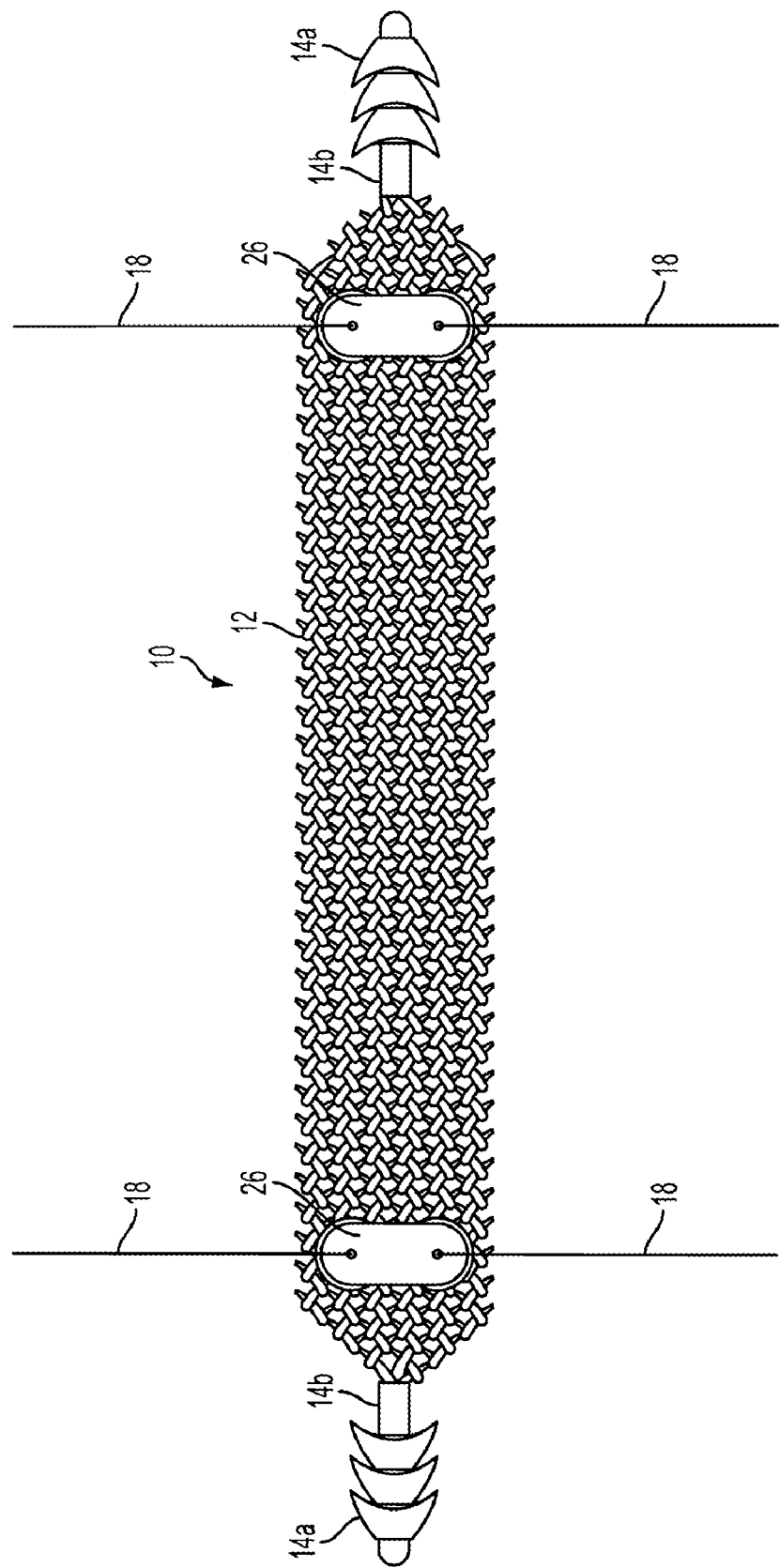
FIG. 3B is a plan view of another embodiment of a medical device for use in treatment of UI, in accordance with systems and methods consistent with the present invention.

Referring to FIG. 3B, a plan view is shown of another embodiment of medical device 10 for use in treatment of UI, in accordance with systems and methods consistent with the present invention. The embodiment of medical device 10 shown in FIG. 3B differs from the embodiment shown in FIGS. 1A-1F by including an aperture 16 and aperture cover 20 that is a shape other than circular (in this case, elliptical, though one may employ any desired shape) and located in proximity to each end of strip 12. The use of an elliptically-shaped aperture 16 and aperture cover 20 (or other shape) may improve holding strength, as compared to a circularly-shaped aperture 16 and aperture cover 20.

Figure 4A:
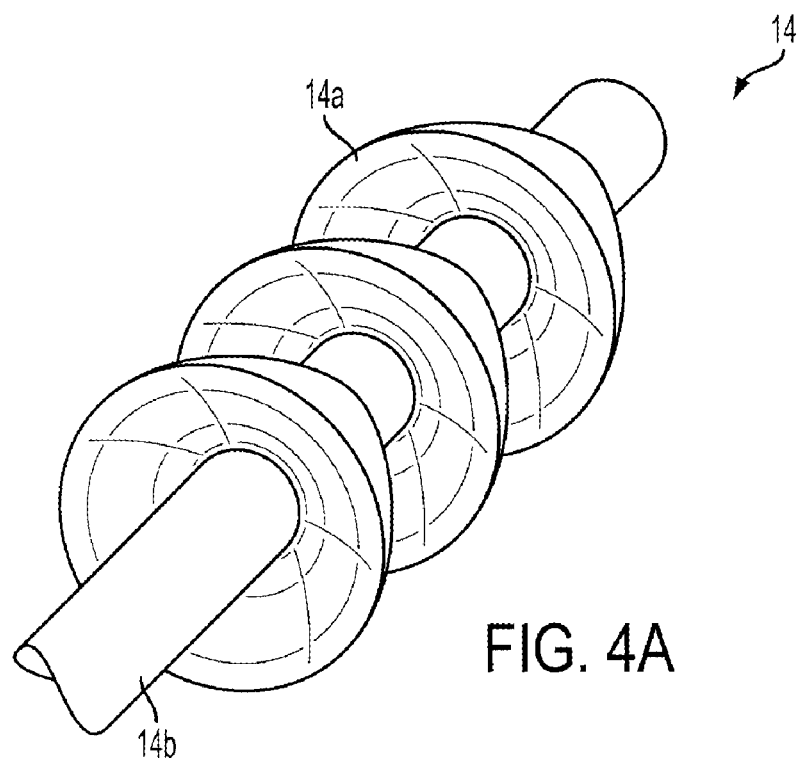
FIG. 4A is a partial perspective view of an embodiment of a fastener for use with any embodiment of a medical device for use in treatment of UI, in accordance with systems and methods consistent with the present invention.

Referring to FIG. 4A, a partial perspective view is shown of an embodiment of a fastener 14 for use with any embodiment of medical device 10 for use in treatment of UI, in accordance with systems and methods consistent with the present invention. Fastener 14, as shown in FIG. 4A, corresponds to fastener 14, as shown in FIGS. 1A-1C, FIGS. 2A-2B and FIGS. 3A-3B. Fastener 14 may include a shaft 14b coupled to an end of strip 12 (not shown) and one or more barbs 14a coupled to shaft 14b. As shown in FIG. 4A, fastener 14 includes a plurality of barbs 14a, however, a single barb 14a may be employed. Additionally, the barbs 14a shown in FIG. 4A traverse the entire perimeter of shaft 14b, however and more generally, fastener 14 and any other fastener that may be employed with medical device 10 may include one or more barbs that traverse only a portion of the perimeter of the respective shaft. Moreover, fastener 14 and any fastener that may be employed with medical device 10 are not limited to the exemplary structures shown in this or any other figure of the application. Simply put, fasteners used with medical device 10 may employ any structure suitable for anchoring the ends of strip 12 into patient tissue.

Figure 4B:
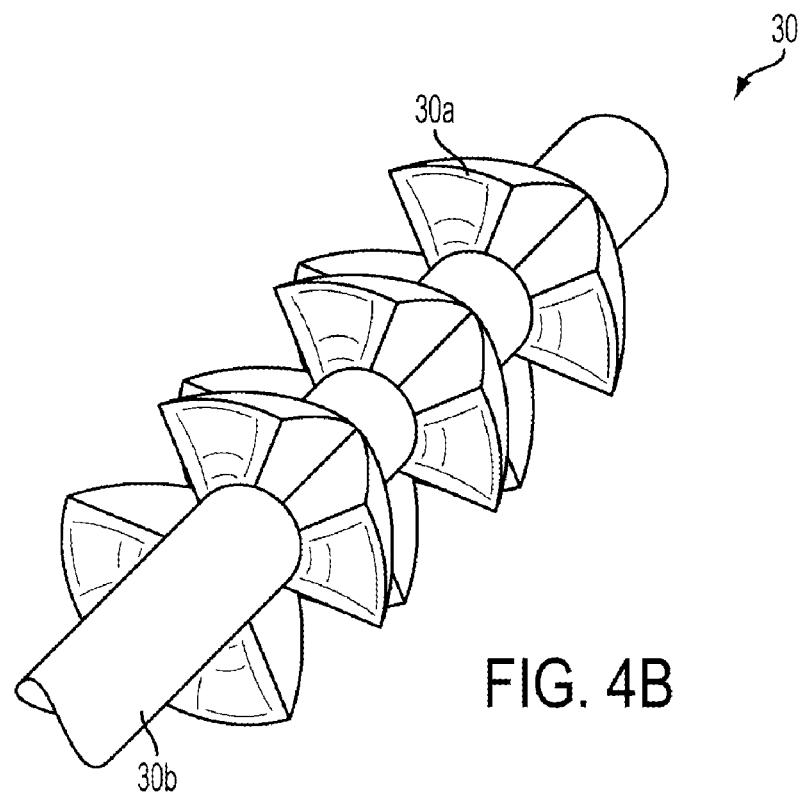
FIG. 4B is a partial perspective view of another embodiment of a fastener for use with any embodiment of a medical device for use in treatment of UI, in accordance with systems and methods consistent with the present invention.

Referring to FIG. 4B, a partial perspective view is shown of another embodiment of a fastener 30 for use with any embodiment of medical device 10 for use in treatment of UI, in accordance with systems and methods consistent with the present invention. Fastener 30 may include a shaft 30b coupled to an end of strip 12 (not shown) and one or more barbs 30a coupled to shaft 30b. As shown in FIG. 4B, fastener 30 includes a plurality of barbs 30a, however, a single barb 30a may be employed. Additionally, the barbs 30a shown in FIG. 4B traverse less than the entire perimeter of shaft 30b, however and more generally, fastener 30 and any other fastener that may be employed with medical device 10 may include one or more barbs that traverse a smaller portion of the perimeter of the respective shaft. Moreover, fastener 30 and any fastener that may be employed with medical device 10 are not limited to the exemplary structures shown in this or any other figure of the application. Simply put, fasteners used with medical device 10 may employ any structure suitable for anchoring the ends of strip 12 into patient tissue.

Figure 4C:
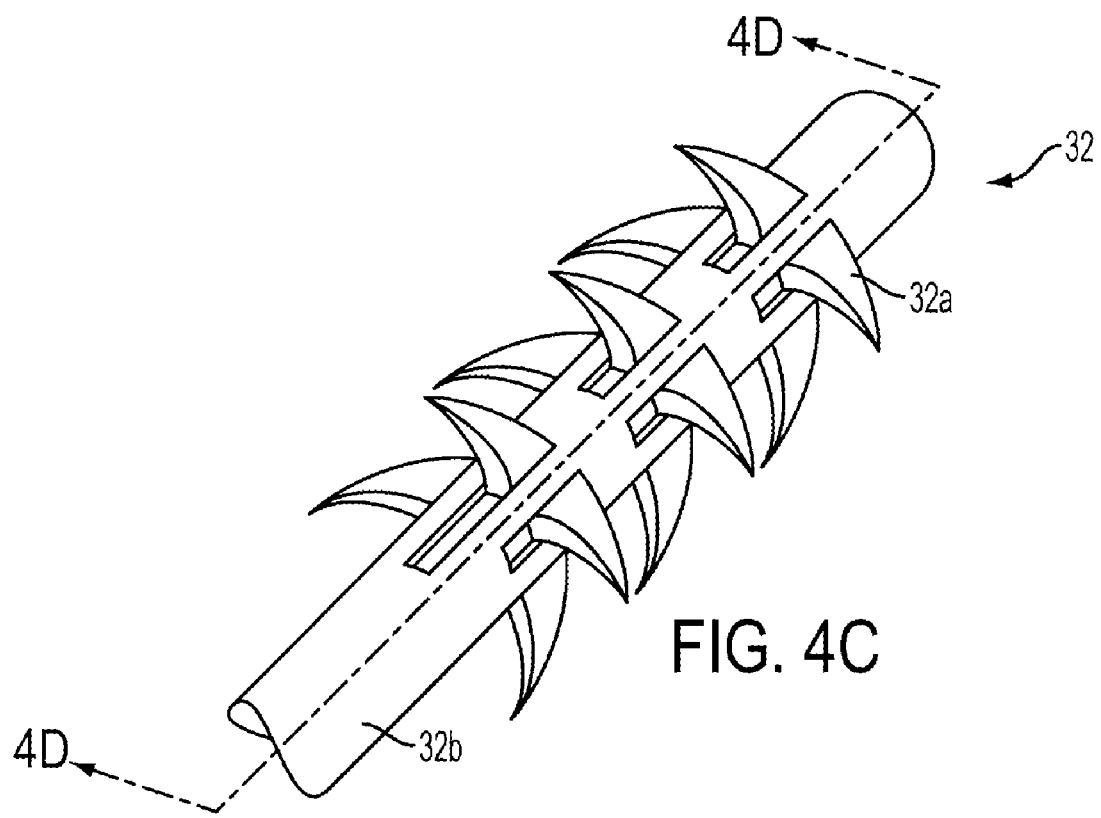
FIG. 4C is a partial perspective view of another embodiment of a fastener for use with any embodiment of a medical device for use in treatment of UI, in accordance with systems and methods consistent with the present invention.

Referring to FIG. 4C, a partial perspective view is shown of another embodiment of a fastener 32 for use with any embodiment of medical device 10 for use in treatment of UI, in accordance with systems and methods consistent with the present invention. Fastener 32 may include a shaft 32b coupled to an end of strip 12 (not shown) and one or more barbs 32a coupled to shaft 32b. As shown in FIG. 4C, fastener 32 includes a plurality of barbs 32a, however, a single barb 32a may be employed. Additionally, the barbs 32a shown in FIG. 4C traverse less than the entire perimeter of shaft 32b, however and more generally, fastener 32 and any other fastener that may be employed with medical device 10 may include one or more barbs that traverse a smaller or greater portion of the perimeter of the respective shaft. Moreover, fastener 32 and any fastener that may be employed with medical device 10 are not limited to the exemplary structures shown in this or any other figure of the application. Simply put, fasteners used with medical device 10 may employ any structure suitable for anchoring the ends of strip 12 into patient tissue. Fastener 32 also represents an exemplary embodiment of a retractable fastener, as will be discussed below with reference to FIGS. 4D and 4E.

Figure 4D:
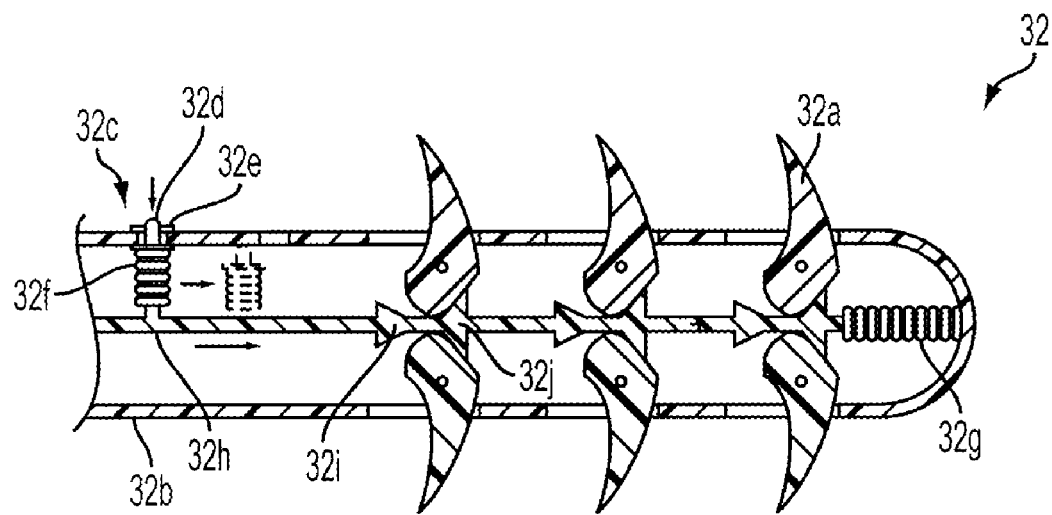
FIGS. 4D and 4E are cross sectional views taken along the line 4D-4D in FIG. 4C, showing an operational sequence for an embodiment of a retractable fastener, in accordance with systems and methods consistent with the present invention.
Figure 4E:
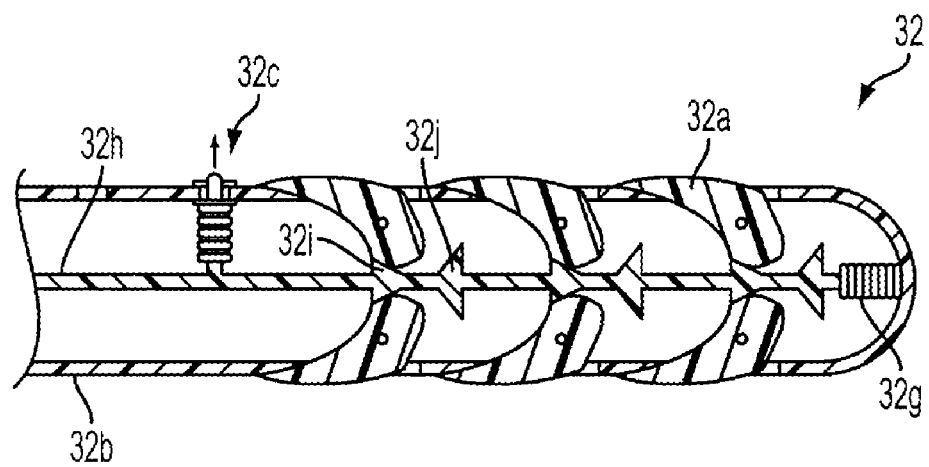

Referring to FIGS. 4D and 4E, cross sectional views are shown taken along the line 4D-4D in FIG. 4C, showing an operational sequence for an embodiment of a retractable barbed fastener 32, in accordance with systems and methods consistent with the present invention. In this exemplary embodiment, a system resides within shaft 32b for deploying and retracting barbs 32a. This system may include an operating mechanism 32c, a drive shaft 32h, barb actuators 32i and 32j and a biasing spring 32g. As shown in FIG. 4D, barbs 32a are deployed, in response to the default position of operating mechanism 32c and biasing spring 32g, i.e., the normal position of fastener 32 is open with barbs 32a deployed. Those skilled in the art appreciate that any retractable fastener employed with medical device 10 may alternatively have a normally closed or retracted fastener. Operating mechanism 32c may include an operating post 32d, a guide member 32e and a spring 32f.

To retract barbs 32a, a medical practitioner depresses operating post 32d such that it depresses spring 32f and moves operating post 32d below the interior wall of shaft 32b. As such guide member 32e, which does not move below the outer wall of shaft 32b, may be moved (to the right in FIG. 4D) along the outer surface of shaft 32b, while operating post 32d slides (to the right in FIG. 4D) within a slot cut into the interior wall of shaft 32b. The medical practitioner may employ a general purpose surgical instrument or a specifically-designed tool to operate operating mechanism 32c, as described, such a tool design being within the capability of those skilled in the art. As guide member 32e continues to move (to the right in FIG. 4D) along the outer surface of shaft 32b, it moves drive shaft 32h, which similarly moves barb actuators 32i and 32j (to the right in FIG. 4D) to compress spring 32g and retract barbs 32a. At a predetermined position located at the end of the interior guide slot for operating post 32d, operating post 32d reaches an aperture in shaft 32b, which frees operating post 32d to pop up in response to an expansion of spring 32f and barbs 32a are retracted, as shown in FIG. 4E.

Using FIG. 4E as a starting point to deploy or redeploy barbs 32a, the medical practitioner depresses operating post 32d such that it depresses spring 32f and moves operating post 32d below the interior wall of shaft 32b. The now-compressed biasing spring 32g expands, moving operating mechanism 32c (to the left in FIG. 4E) until reaching a predetermined position located at the opposing end of the interior guide slot for operating post 32d. At this point, operating post 32d reaches an aperture in shaft 32b, which frees operating post 32d to pop up in response to an expansion of spring 32f, deploying barbs 32a, as shown in FIG. 4D.

For the sake of clarity, the system set forth above for providing a retractable fastener 32 is merely exemplary. Moreover, it is well within the skills of persons in the art to create a wide variety of retractable fasteners, any of which may be employed with any embodiment of medical device 10.

Figure 4F:
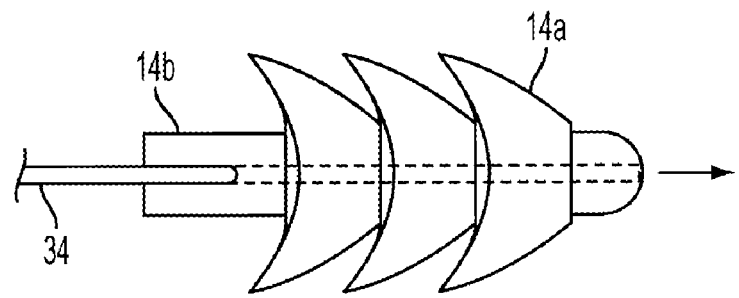
FIGS. 4F-4H are partial elevation views of embodiments of fasteners for use with any embodiment of a medical device for use in treatment of UI, in accordance with systems and methods consistent with the present invention.
Figure 4G:
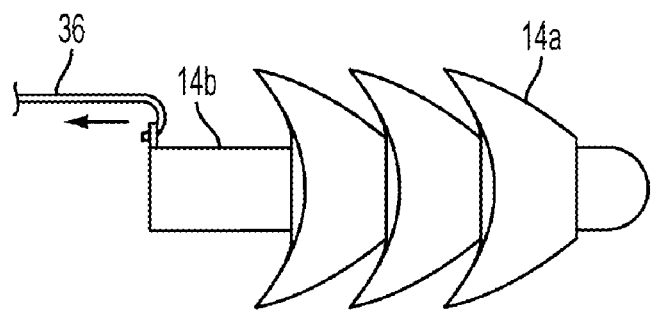
Figure 4H:
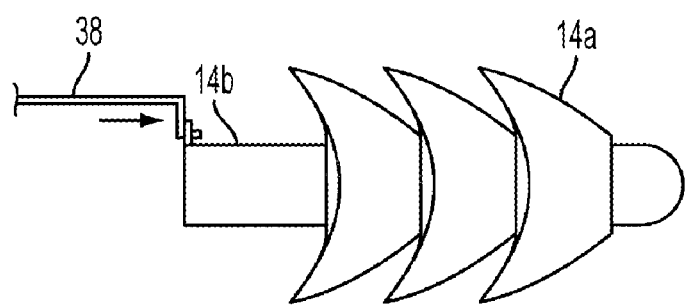

Referring to FIGS. 4F-4H, partial elevation views are shown of embodiments of fasteners 14 for use with any embodiment of medical device 10 for use in treatment of UI, in accordance with systems and methods consistent with the present invention. FIGS. 4F-4H also show exemplary tools 34-38 for inserting and/or extracting a fastener 14. In FIG. 4F, tool 34 is inserted within shaft 14b to drive barbs 14a into patient tissue, thereby inserting fastener 14. While not explicitly shown in FIG. 4F, those skilled in the art appreciate that tool 34 may be employed to disengage Fastener 14, as well, using any one of a variety of different designs within the level of experience of those skilled in the art. In FIG. 4G, tool 36 engages a position along shaft 14b for extracting fastener 14 (whether barbs 14 are retractable or not). In FIG. 4H, tool 38 engages a position along shaft 14b to drive barbs 14a into patient tissue, thereby inserting fastener 14. For the sake of clarity, the tools 34-38 set forth above for inserting and/or extracting fastener 14 (or any other fastener) are exemplary. Moreover, it is well within the skill level of those persons skilled in the art to create a wide variety of tools for inserting and/or extracting fastener 14 (or any other fastener), any of which may be employed with any embodiment of medical device 10.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for treating urinary incontinence (UI), the system comprising:
   a strip of mesh having a primary axis and a secondary axis orthogonal to and coplanar with the primary axis; a first end and a second end, the first end and the second end being located at opposite ends of the primary axis; a first surface located on a first side of the strip, said first surface for providing support to the urethra of a patient under treatment for UI; and a second surface located on a second side of the strip opposite the first surface;
   a first fastener including at least one barb, said first fastener coupled to the first end of the strip;
   a second fastener including at least one barb, said second fastener coupled to the second end of the strip;
   a plurality of cords, each cord of the plurality of cords coupled to the strip for extracting the strip when desired;
   a first aperture in the second surface of the strip and located closer to the first end of the strip than to the second end of the strip, a diameter of the first aperture exceeding a diameter of any aperture in a regular pattern of apertures formed by the mesh; and
   a second aperture in the second surface of the strip and located closer to the second end of the strip than to the first end of the strip, a diameter of the second aperture exceeding the diameter of any aperture in the regular pattern of apertures formed by the mesh,
   wherein the first aperture and the second aperture do not extend through the first surface of the strip,
   wherein the mesh forms a first support shelf in the first aperture and a second support shelf in the second aperture, each support shelf being closer to the first surface of the strip than to second surface of the strip.

2. The system of claim 1 wherein the strip comprises a sling for treatment of UI.

3. The system of claim 1 wherein the strip comprises a synthetic mesh material, a mesh of biomaterial or a combination thereof.

4. The system of claim 1 wherein each fastener includes:
   a shaft from which protrudes the at least one barb; and
   a location for receiving a portion of a provided tool used to insert the respective fastener into tissue of the patient.

5. The system of claim 4 wherein each barb extends continuously around the circumference of its respective shaft.

6. The system of claim 4 wherein each barb does not extend continuously around the circumference of its respective shaft.

7. The system of claim 1 wherein each barb is retractable between a deployed position for engagement with the tissue of the patient and a retracted position for disengagement from the tissue of the patient.

8. The system of claim 1 further comprising one or more additional fasteners coupled to each end of the strip.

9. The system of claim 1 wherein:
   at least one cord of the plurality of cords includes a first end coupled to the first support shelf and a second free end for use in extracting the strip when desired; and
   at least one cord of the plurality of cords includes a first end coupled to the second support shelf and a second free end for use in extracting the strip when desired.

10. The system of claim 1 wherein:
    at least one cord of the plurality of cords includes a first end coupled to the first support shelf and a second end coupled the first support shelf, thereby forming a first loop for use in extracting the strip when desired; and
    at least one cord of the plurality of cords includes a first end coupled to the second support shelf and a second end coupled the second support shelf, thereby forming a second loop for use in extracting the strip when desired.

11. The system of claim 10 further comprising:
    a first aperture cover having a plurality of apertures, the at least one cord coupled to the first support shelf, passing through the apertures in the first aperture cover and for tying to secure the first aperture cover against the first support shelf after severing the first loop; and
    a second aperture cover having a plurality of apertures, the at least one cord coupled to the second support shelf, passing through the apertures in the second aperture cover and for tying to secure the second aperture cover against the second support shelf after severing the second loop.

12. The system of claim 11 wherein the distance between the apertures in the first aperture cover is no less than the radius of the first aperture cover and the distance between the apertures in the second aperture cover is no less than the radius of the second aperture cover.

13. The system of claim 11 wherein the first aperture cover and the second aperture cover are both more rigid than the mesh.

14. The system of claim 11 wherein the strip of mesh, the first fastener, the second fastener, the plurality of cords, the first aperture cover and the second aperture cover comprise an integral structure.

15. The system of claim 1 further comprising:
one or more additional apertures in the strip and located closer to the first end of the strip than to the second end of the strip, a diameter of the one or more additional apertures exceeding the diameter of any aperture in the regular pattern of apertures formed by the mesh; and
one or more additional apertures in the strip and located closer to the second end of the strip than to the first end of the strip, a diameter of the one or more additional apertures exceeding the diameter of any aperture in the regular pattern of apertures formed by the mesh.

16. The system of claim 1 wherein the first aperture and the second aperture each have a cross sectional shape including one or more of a portion that is straight and a portion that is curved.

17. The system of claim 16 wherein the cross sectional shape of the first aperture and the cross sectional shape of the second aperture is one of a circle and an ellipse.

18. The system of claim 16 wherein the center of the cross sectional shape of the first aperture and the center of the cross sectional shape of the second aperture intersects the primary axis.

19. The system of claim 16 wherein the cross sectional shape of the first aperture and the cross sectional shape of the second aperture is an ellipse and a major axis of the ellipse is orthogonal to the primary axis.

20. The system of claim 1 further comprising:
a first plurality of protrusions coupled to and extending from the first surface of the strip and arranged in an array located in proximity to the first aperture in the strip, the first plurality of protrusions shaped to engage with the tissue of the patient; and
a second plurality of protrusions coupled to and extending from the first surface of the strip and arranged in an array located in proximity to the second aperture in the strip, the second plurality of protrusions shaped to engage with the tissue of the patient.

21. The system of claim 1 wherein the plurality of cords includes one or more cords attached to a first region of the strip and one or more cords attached to a second region of the strip such that pulling of the one or more cords attached to the first region of the strip and the one or more cords attached to the second region of the strip will permit extraction of the strip without damage to the strip.

22. The system of claim 21 wherein the first region of the strip is closer to the first end of the strip than to the second end of the strip and the second region of the strip is closer to the second end of the strip than to the first end of the strip.

23. The system of claim 21 wherein the first region of the strip is located in proximity to the first end of the strip and the second region of the strip is located in proximity to the second end of the strip.

* * * * *